US00PP26965P2

(12) United States Plant Patent
Dummen

(10) Patent No.: US PP26,965 P2
(45) Date of Patent: Jul. 19, 2016

(54) ***PELARGONIUM* PLANT NAMED 'DUEGBOFM14'**

(50) Latin Name: *Pelargonium peltatum*
Varietal Denomination: Duegbofm14

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 157 days.

(21) Appl. No.: 14/120,827

(22) Filed: Jul. 1, 2014

(51) Int. Cl.
*A01H 5/02* (2006.01)

(52) U.S. Cl.
USPC ..... Plt./332

(58) Field of Classification Search
USPC ..... Plt./332
See application file for complete search history.

*Primary Examiner* — Keith Robinson
(74) *Attorney, Agent, or Firm* — C. A. Whealy

(57) ABSTRACT

A new and distinct cultivar of Ivy Geranium plant named 'Duegbofm14', characterized by its upright to outwardly spreading and rounded plant habit; vigorous growth habit; freely basal branching habit; freely flowering habit; large dark red-colored double flowers; and good garden performance.

1 Drawing Sheet

Botanical designation: *Pelargonium peltatum.*
Cultivar denomination: 'DUEGBOFM14'.

BACKGROUND OF THE INVENTION

The present invention relates to a new and distinct cultivar of Ivy Geranium plant, botanically known as *Pelargonium peltatum*, and hereinafter referred to by the name 'Duegbofm14'.

The new Ivy Geranium plant is a product of a planned breeding program conducted by the Inventor in Rheinberg, Germany. The objective of the breeding program is to create new vigorous Ivy Geranium plants with numerous attractive flowers.

The new Ivy Geranium plant originated from a cross-pollination made by the Inventor in July, 2010 in Rheinberg, Germany of a proprietary selection of *Pelargonium peltatum* identified as code number P05-4113-009, not patented, as the female, or seed, parent with a proprietary selection of *Pelargonium peltatum* identified as code number F-018-1618, not patented, as the male, or pollen, parent. The new Ivy Geranium plant was discovered and selected by the Inventor as a single flowering plant from within the progeny of the stated cross-pollination in a controlled greenhouse environment in Rheinberg, Germany in May, 2013.

Asexual reproduction of the new Ivy Geranium plant by vegetative terminal cuttings in a controlled greenhouse environment in Rheinberg, Germany since June, 2013 has shown that the unique features of this new Ivy Geranium plant are stable and reproduced true to type in successive generations.

SUMMARY OF THE INVENTION

Plants of the new Ivy Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duegbofm14'. These characteristics in combination distinguish 'Duegbofm14' as a new and distinct Ivy Geranium plant:

1. Upright to outwardly spreading and rounded plant habit.
2. Vigorous growth habit.
3. Freely basal branching habit.
4. Freely flowering habit.
5. Large dark red-colored double flowers.
6. Good garden performance.

Plants of the new Ivy Geranium differ primarily from plants of the female parent selection in flower color as plants of the female parent selection have lavender-colored flowers.

Plants of the new Ivy Geranium differ primarily from plants of the male parent selection in flower color as plants of the male parent selection have lighter red-colored flowers. In addition, plants of the new *Pelargonium* are more vigorous than plants of the male parent selection.

Plants of the new Ivy Geranium can be compared to plants of *Pelargonium peltatum* 'Duegbofmer', disclosed in U.S. Plant Pat. No. 26,103. In side-by-side comparisons conducted in Rheinberg, Germany, plants of the new Ivy Geranium differed primarily from plants of 'Duegbofmer' in the following characteristics:

1. Plants of the new Ivy Geranium were larger than plants of 'Duegbofmer'.
2. Plants of the new Ivy Geranium had smaller leaves than plants of 'Duegbofmer'.
3. Plants of the new Ivy Geranium were more freely flowering than plants of 'Duegbofmer'.
4. Plants of the new Ivy Geranium and 'Duegbofmer' differed slightly in flower color.
5. Plants of the new Ivy Geranium had shorter and slightly thicker peduncles than plants of 'Duegbofmer'.

BRIEF DESCRIPTION OF THE PHOTOGRAPH

The accompanying colored photograph illustrates the overall appearance of the new Ivy Geranium plant showing the colors as true as it is reasonably possible to obtain in colored reproductions of this type. Colors in the photograph may differ slightly from the color values cited in the detailed botanical description which accurately describe the colors of the new Ivy Geranium plant.

The photograph comprises a side perspective view of a typical flowering plant of 'Duegbofm14' grown in a container.

DETAILED BOTANICAL DESCRIPTION

The aforementioned photograph and following observations and measurements describe plants grown during the summer in 12-cm containers in a glass-covered greenhouse in Rheinberg, Germany and under cultural practices typical of commercial *Pelargonium* production. During the production of the plants, day and night temperatures averaged 18° C. and light levels averaged 4,500 lux. Plants were pinched one time three weeks after planting and were 13 weeks old when the photograph and the description were taken. In the detailed description, color references are made to The Royal Horticultural Society Colour Chart, 2007 Edition, except where general terms of ordinary dictionary significance are used.

Botanical classification: *Pelargonium peltatum* 'Duegbofm14'.

Parentage:

*Female, or seed, parent*.—Proprietary selection of *Pelargonium peltatum* identified as code number P05-4113-009, not patented.

*Male or pollen parent*.—Proprietary selection of *Pelargonium peltatum* identified as code number F-018-1618, not patented.

Propagation:

*Type*.—By vegetative terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous.

*Rooting habit*.—Freely branching; dense.

Plant description:

*Plant and growth habit*.—Upright to outwardly spreading and rounded plant habit; uniformly rounded; densely foliated; vigorous growth habit.

*Branching habit*.—Freely basal branching habit with about five to six basal branches developing per plant.

*Plant height to top of flower umbels*.—About 26 cm.

*Plant height to top of foliar plane*.—About 20 cm.

*Plant width*.—About 90 cm.

*Lateral branches*.—Length: About 31 cm. Diameter: About 6 mm. Internode length: About 3.1 cm. Texture: Pubescent. Strength: Moderately strong. Color: Close to 144A.

Leaf description:

*Arrangement*.—Alternate; simple.

*Length*.—About 3.5 cm.

*Width*.—About 3.7 cm.

*Shape*.—Roughly reniform; palmately lobed.

*Apex*.—Lobe apices, acute.

*Base*.—Cordate.

*Margin*.—Crenate.

*Venation pattern*.—Palmate.

*Texture, upper surface*.—Pubescent.

*Texture, lower surface*.—Smooth, glabrous.

*Color*.—Developing and fully expanded leaves, upper surface: Close to 137A; venation, close to 137A. Developing and fully expanded leaves, lower surface: Close to 143C; venation, close to 143C.

*Zonation pattern*.—Distance from margin: About 1.6 cm. Width: About 7.2 mm. Color: Close to 166A.

*Petioles*.—Length: About 3.4 cm. Diameter: About 2.2 mm. Texture, upper and lower surfaces: Smooth, glabrous. Color, upper and lower surfaces: Close to 144A.

Flower description:

*Flower arrangement*.—Double type flowers arranged in rounded hemispherical umbels arising from apical leaf axils; umbels displayed above the foliar plane on moderately strong peduncles; flowers face mostly upright to outwardly depending on position in the inflorescence.

*Fragrance*.—None detected.

*Flowering habit*.—Freely flowering habit, about seven to eight flowers per umbel and potentially about 38 flower umbels developing per plant.

*Flowering season*.—Year-round under greenhouse conditions; in outdoor nurseries and gardens in Germany, flowering is continuous from spring throughout the summer until the autumn; plants begin to flower about eight weeks after planting.

*Flower longevity*.—Individual flowers last about five to seven days on the plant; flowers persistent.

*Umbel height*.—About 5.4 cm.

*Umbel diameter*.—About 7.9 cm.

*Flower diameter*.—About 4 cm by 4.3 cm.

*Flower depth* (*height*).—About 1.8 cm.

*Flower buds*.—Length: About 1.2 cm. Diameter: About 6.4 mm. Shape: Ovoid. Color: Close to 53A.

*Petals*.—Quantity per flower: About five arranged in a single whorl. Length: About 2.6 cm. Width: About 1.4 cm. Shape: Obovate. Apex: Rounded. Base: Attenuate. Margin: Sinuate. Texture, upper and lower surfaces: Smooth, glabrous. Color: When opening and fully opened, upper surface: Close to 53A; color becoming closer to 187A with development. When opening and fully opened, lower surface: Close to 53C; color becoming closer to 187A with development.

*Petaloids*.—Quantity per flower: About three to five arranged in a single whorl. Length: About 1.4 cm. Width: About 6.6 mm. Shape: Obovate. Apex: Rounded. Base: Attenuate. Margin: Sinuate. Texture, upper and lower surfaces: Smooth, glabrous. Color: When opening and fully opened, upper surface: Close to 53A. When opening and fully opened, lower surface: Close to 53C.

*Sepals*.—Quantity per flower: About five arranged in a single whorl. Length: About 1.1 cm. Width: About 3.6 mm. Shape: Ensiform. Apex: Apiculate. Margin: Entire. Texture, upper and lower surfaces: Smooth, glabrous. Color, upper and lower surfaces: Close to 144A.

*Peduncles* (*umbel stems*).—Length: About 6.7 cm. Diameter: About 3.6 mm. Strength: Moderately strong. Texture: Smooth, glabrous. Color: Close to 144A.

*Pedicels* (*individual flower stems*).—Length: About 2.1 cm. Diameter: About 1.8 mm. Strength: Moderately strong. Texture: Smooth, glabrous. Color: Close to 144A.

*Reproductive organs*.—Androecium: Stamen quantity per flower: Three to five. Filament length: About 9 mm. Filament color: Close to 155C. Anther length: About 2 mm. Anther shape: Oblong. Anther color: Close to 187A. Pollen amount: Moderate. Pollen color: Close to 28A. Gynoecium: Pistil quantity per flower: One. Pistil length: About 1.3 cm. Stigma shape: Tapering. Stigma color: Close to 185A. Style length: About 2 mm. Style color: Close to 155B. Ovary color: Close to 145D.

*Seeds and fruits*.—Seed and fruit development have not been observed on plants of the new Ivy Geranium.

Disease & pest resistance: Plants of the new Ivy Geranium have not been observed to be resistant to pathogens and pests common to Ivy Geranium plants.

Garden performance: Plants of the new Ivy Geranium have been observed have good garden performance and to tolerate rain, wind, and temperatures ranging from about 5° C. to about 40° C.

It is claimed:

1. A new and distinct Ivy Geranium plant named 'Duegbofm14' as illustrated and described.

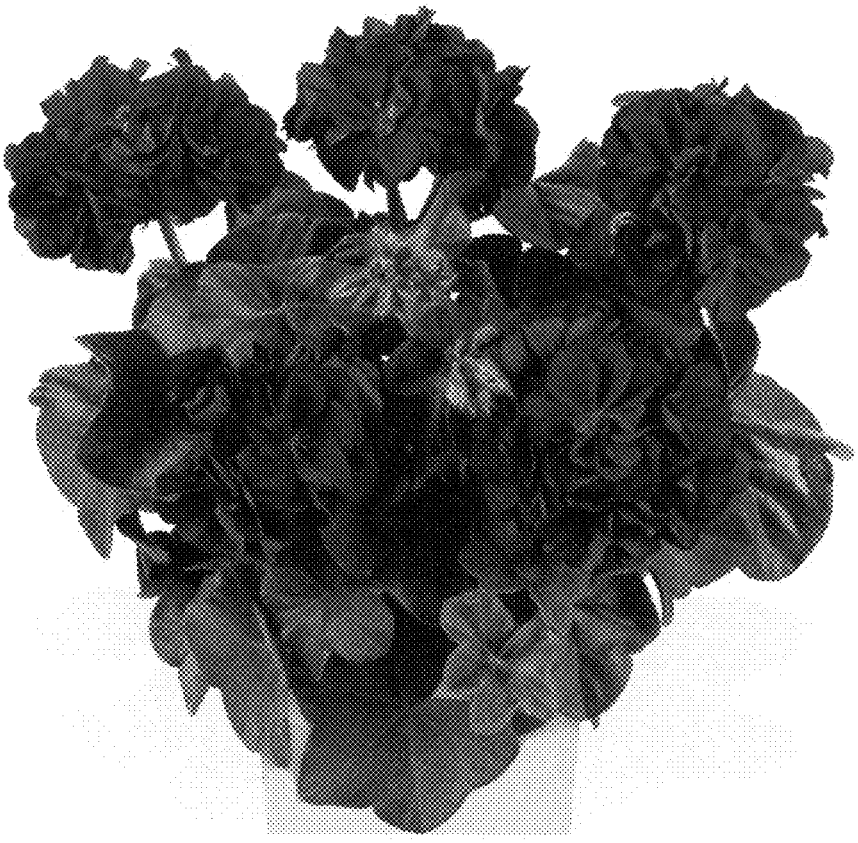

* * * * *